US00PP09652P

United States Patent [19]

Meilland

[11] Patent Number: Plant 9,652

[45] Date of Patent: Oct. 8, 1996

[54] MINIATURE ROSE PLANT NAMED 'MEIFERJAC'

[75] Inventor: Alain A. Meilland, Antibes, France

[73] Assignee: The Conard-Pyle Company, West Grove, Pa.

[21] Appl. No.: 555,733

[22] Filed: Nov. 9, 1995

[51] Int. Cl.[6] ..... A01H 5/00

[52] U.S. Cl. ..... Plt./10

[58] Field of Search ..... Plt./7.1, 9, 10, Plt./10.1

*Primary Examiner*—Howard J. Locker

*Attorney, Agent, or Firm*—Burns, Doane, Swecker & Mathis, L.L.P.

[57] ABSTRACT

A new and distinct variety of rose plant of the miniature class is provided which abundantly forms attractive small red flowers which are stable and well retain their coloration upon the passage of time. The plant is erect and exhibits a compact and regular growth habit. The blossoms possess no fragrance. The plant can be grown as attractive ornamentation in the landscape or as a decorative pot plant.

1 Drawing Sheet

SUMMARY OF THE INVENTION

The new variety of miniature rose plant was created by artificial pollination wherein two parents were crossed which previously had been studied in the hope that they would contribute the desired characteristics. The female parent (i.e., the seed parent) of the new variety was the product of the pollination of the 'Bonfire Night' variety (non-patented in the United States) and the 'Meininrut' variety (non-patented in the United States). The male parent (i.e., the pollen parent) of the new variety was the 'Orange Jewel' variety (non-patented in the United States). The parentage of the new variety can be summarized as follows:

('Bonfire Night'×'Meininrut')×'Orange Jewel'.

The seeds resulting from the above pollination were sown and small plants were obtained which were physically and biologically different from each other. Selective study resulted in the identification of a single plant of the new variety.

It was found that the new variety of Miniature rose plant of the present invention possesses the following combination of characteristics:

(a) forms in abundance attractive small double flowers which exhibit a stable red coloration,
(b) exhibits an erect, compact, and regular growth habit, and
(c) is particularly suited for growing as an ornamental pot plant.

The new variety well meets the needs of the horticultural industry. It is particularly well-suited for use as attractive ornamentation in the landscape or for growing as a decorative pot plant.

The new variety has been found to undergo asexual propagation in France by a number of routes, including budding, grafting, and cuttage. Asexual propagation by the above- mentioned methods as performed in France has shown that the characteristics of the new variety are strictly transmissible from one generation to another.

The new variety has been named the 'Meiferjac' variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were one year of age and were observed during September while growing on their own roots indoors at LeCannet des Maures, Var, France.

FIG. 1 — illustrates a specimen of a young shoot;

FIG. 2 — illustrates specimens of two floral buds before the opening of the sepals;

FIG. 3 — illustrates specimens of two floral buds at the opening of the sepals;

FIG. 4 — illustrates specimens of two floral buds at the opening of the petals;

FIG. 5 — illustrates specimens of two flowers during the course of opening;

FIG. 6 — illustrates a specimen of an open flower — plan view — obverse;

FIG. 7 — illustrates a specimen of an open flower — plan view — reverse;

FIG. 8 — illustrates a specimen of a fully open flower — plan view — obverse;

FIG. 9 — illustrates a specimen of a fully open flower — plan view — reverse;

FIG. 10 — illustrates a specimen of a floral receptacle showing the arrangement of the stamens and pistils;

FIG. 11 — illustrates a specimen of a floral receptacle showing the arrangement of the pistils (stamens removed);

FIG. 12 — illustrates a specimen of a flowering stem;

FIG. 13 — illustrates a specimen of a main branch;

FIG. 14 — illustrates specimens of leaves with three leaflets with the upper surface being shown at the right and the under surface being shown at the left;

FIG. 15 — illustrates specimens of leaves with five leaflets with the upper surface being shown at the top and the under surface being shown at the bottom; and FIG. 16 — illustrates specimens of leaves with seven leaflets with the upper surface being shown at the bottom-left and the under surface being shown at the upper-right.

DETAILED DESCRIPTION

Figures 1, 2, 3, 4, 5, 6, 7, 8, 9, 10, 11, 12, 13, 14, 15, 16:
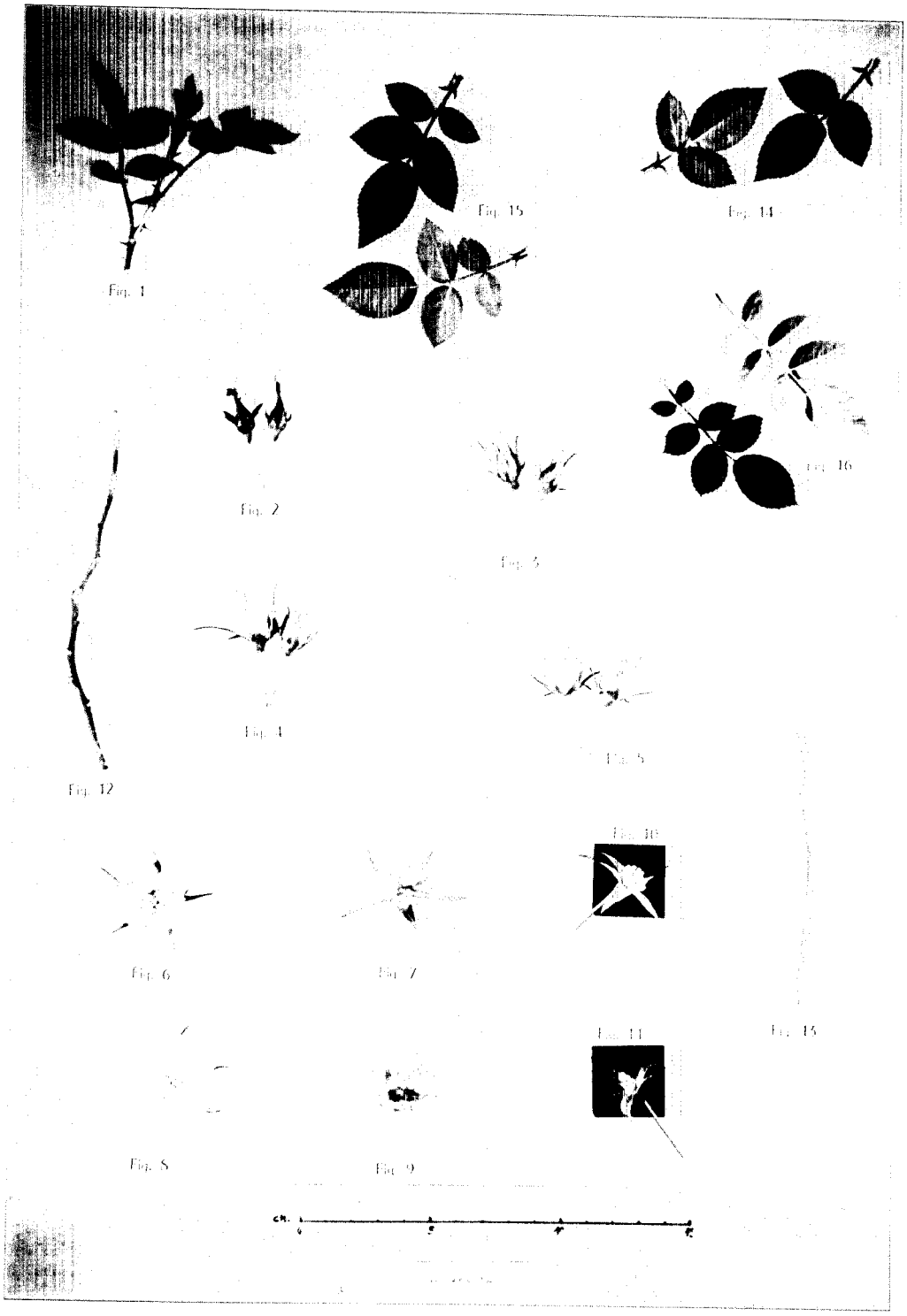

The chart used in the identification of the colors is that of The Royal Horticultural Society (R.H.S. Colour Chart). The terminology which precedes reference to the chart has been added to indicate the corresponding colors in more common terms. The description is based on one year-old specimens of the new variety which were observed during September while growing on their own roots indoors at LeCannet des Maures, Var, France.

Class: Miniature.

Plant:

*Height.*—Approximately 30 cm. on average at the end of the growing season.

*Habit.*—Erect, compact and regular.

Branches:

*Color.*—Young stems: Lettuce Green, Yellow-Green Group 144A. Adult wood: dark Lettuce Green, Yellow-Green Group 144A.

*Thorns.*—Size: small. Quantity: moderately numerous. Color: pinkish.

Leaves:

*Petioles.*—Upper surface: striped, reddish on young foliage and medium green on mature foliage with more or less glandular edges. Under surface: light green and bear some small thorns.

*Stipules.*—Adnate, pectinate, rather narrow and linear.

*Leaflets.*—Number: 3, 5, and 7 (most often). Shape: elliptic. Texture: consistent. General appearance: dense, medium green, and semi-glossy foliage. Color (young foliage): upper surface: Lettuce Green, Yellow-Green Group 144A and lightly suffused and edged with reddish-brown coloration. under surface: Lettuce Green, Yellow-Green Group 144A and suffused with reddish-brown coloration. Color (adult foliage): upper surface: dark green, Yellow-Green Group 147A. under surface: dark green, Yellow-Green Group 147A and suffused with Greyed-Green Group 194A.

Inflorescence:

*Number of flowers.*—Multiflorous, and commonly with approximately 6 to 15 flowers per stem.

*Peduncle.*—Medium green in coloration, more or less glandular, and the length is approximately 3.5 cm. on average.

*Sepals.*—Upper surface: tomentose and greenish in coloration. Under surface: medium green.

*Buds.*—Shape: conical. Length: approximately 2 cm. on average. Size: small. Color upon opening: Color upon opening: upper surface: Vermillion Red, Red Group 44A with the base of the petal being yellow. under surface: medium red, Red Group 42A with the base of the petal being yellow.

*Flower.*—Form: cupped with somewhat parallel sides. Diameter: approximately 4 cm. on average. Color (when opening begins): upper surface: Dutch Vermillion, Red Group 40A, with the base of the petal being yellow. under surface: Blood Red, Red Group 45D, with the base of the petal being yellow. Color (when blooming): upper surface: Dutch Vermillion, Red Group 40A, with the base of the petal being yellow. under surface: Blood Red, Red Group 45D, with the base of the petal being yellow. Color (at end of blooming): upper surface: Dutch Vermillion, Red Group 40A, with the base of the petal being yellow. under surface: Blood Red, Red Group 45D, with the base of the petal being yellow. Fragrance: none. Petal number: approximately 27 on average. Petal shape: oval with an obtuse base. Petal drop: good. Anthers: normal and ochre in coloration. Stamen number: approximately 77 on average. Filaments: normal and yellowish in coloration. Pistil number: approximately 52 on average. Stigmas: greenish in coloration. Styles: greenish in coloration. Receptacle: medium green, smooth, and in longitudinal section in the shape of a funnel.

Development:

*Vegetation.*—Strong.

*Blooming.*—Abundant.

*Resistance to diseases.*—Very good.

I claim:

1. A new and distinct variety of Miniature rose plant characterized by the following combination of characteristics:

(a) forms in abundance attractive small double flowers which exhibit a stable red coloration, (b) exhibits an erect, compact, and regular growth habit, and (c) is particularly suited for growing as an ornamental pot plant;

substantially as herein shown and described.

* * * * * cm.